United States Patent [19]

Nielsen-Kahn et al.

[11] Patent Number: 6,096,511

[45] Date of Patent: Aug. 1, 2000

[54] PROTEIN ELONGATION FACTOR 2 AS A TARGET FOR ANTIFUNGAL AND ANTIPARASITIC AGENTS

[75] Inventors: Jennifer Nielsen-Kahn, East Brunswick; Michael C. Justice, Bound Brook; Dennis M. Schmatz, Cranford; Ming-Jo Hsu; Theresa W. Ku, both of Edison, all of N.J.

[73] Assignee: Merck & Co., Inc., Rahway, N.J.

[21] Appl. No.: 09/089,307

[22] Filed: Jun. 2, 1998

Related U.S. Application Data

[60] Provisional application No. 60/049,271, Jun. 10, 1997.

[51] Int. Cl.$^7$ .................. C12Q 1/18; C12N 1/15
[52] U.S. Cl. .................. 435/32; 435/172.3; 435/254.11; 435/255.2
[58] Field of Search .................. 435/32, 172.3, 435/254.1, 255.2, 254.11; 935/68

[56] References Cited

U.S. PATENT DOCUMENTS

| | | | |
|---|---|---|---|
| 3,432,598 | 3/1969 | Sigg et al. ............... | 424/122 |
| 4,492,700 | 1/1985 | Friedman ............... | 424/250 |
| 5,104,852 | 4/1992 | Kralick et al. ............... | 514/6 |
| 5,403,713 | 4/1995 | Bevilaqua et al. ............... | 435/7.1 |
| 5,614,488 | 3/1997 | Bacha ............... | 514/2 |
| 5,641,627 | 6/1997 | Moehle ............... | 435/6 |
| 5,817,502 | 10/1998 | Ligon et al. . | |

FOREIGN PATENT DOCUMENTS

| | | | |
|---|---|---|---|
| WO92/03455 | 3/1992 | WIPO . | |
| WO96/14326 | 5/1996 | WIPO ............... | C07H 15/24 |
| WO96/14327 | 5/1996 | WIPO ............... | C07H 15/24 |
| WO98/11891 | 3/1998 | WIPO ............... | A61K 31/35 |
| WO98/15178 | 4/1998 | WIPO ............... | A01N 37/00 |

OTHER PUBLICATIONS

Mander et al., J. Org. Chem., vol. 56, pp. 3595–3601 (1991).
Hauser et al., Helvetica Chimica Acta, vol. 54, Fasc. % (1971)—Nr. 19–120, pp. 1178–1190.
Kato et al., J. Chem. Soc., Chem, Commun. (1993), pp. 1002–1006.
Phan et al., J. of Biol. Chem., vol. 268, No. 12, pp. 8665–8668 (Apr. 1993).
Jones et al. Molecular and Biochemical Parasitology, vol. 71, pp. 143–147, (1995). No Month Found.
Perentesis et al. Saccharomyces cerevisiae Elongation Factor 2. Biol. Chem. 267 (2), pp. 1190–1197 (Jan. 1992).
Kimata et al. Elongation Factor 2 Mutants Deficient in Diphthamide Formation Show Temperature–sensitive Cell Growth. J. Biol. Chem. 269 (18), pp. 13497–13501. (May 1994).
Justice et al. Elongation factor 2 as a novel target for selective inhibition of fungal protein synthesis. J. Biological Chemistry, 273 (6), pp. 3148–3151. Feb. 6, 1998.

*Primary Examiner*—Ralph Gitomer
*Assistant Examiner*—Marjorie A. Moran
*Attorney, Agent, or Firm*—Elliot Korsen; Mark R. Daniel

[57] ABSTRACT

Inhibition of protein elongation factor 2 provides a target for identifying potential antifungal and antiparasitic compounds. EF2 inhibitors are useful as therapeutic agents against fungal and parasitic infections.

7 Claims, No Drawings

6,096,511

PROTEIN ELONGATION FACTOR 2 AS A TARGET FOR ANTIFUNGAL AND ANTIPARASITIC AGENTS

Priority is claimed under 35 USC 119(e) to provisional application 60/049,271, filed Jun. 10, 1997.

BACKGROUND OF THE INVENTION

Elongation factor 2 (EF2) is an essential protein catalysing ribosomal translocation during protein synthesis in eukaryotic cells. It is highly conserved in all eukaryotes, and has been found to be largely interchangeable in vitro protein synthesis systems reconstituted from such divergent organisms as human, wheat germ, and fungi. Despite the ubiquitous nature of EF2 in eukaryotic systems and the high degree of amino acid sequence homology between EF2s from various eukaryotic systems, a class of compounds, the sordarins, have now been identified to be selective inhibitors of fungal protein synthesis via a selective interaction with fungal EF2. This finding demonstrates the potential for developing pathogen selective EF2 inhibitors which can kill invading organisms while sparing the host of any detrimental effects. Prior to this invention, EF2 has not been considered as a differential target for antifungal or antiparasitic agents.

SUMMARY OF THE INVENTION

The present invention relates to elongation factor 2 (hereinafter referred to as "EF2") as a target for antifungal and antiparasitic agents. In particular, the invention relates to a method for identifying potential antifungal and antiparasitic agents by determining whether a test compound is capable of specifically inhibiting pathogenic protein synthesis via a selective interaction with pathogen EF2. The present invention describes the use of mechanism based assays with or without the use of a transformed eukaryotic organism with a heterologous EF2 to facilitate drug discovery. Additionally, the invention relates to a method for treating fungal infections by administering to a host suffering from a fungal or parasitic infection a therapeutically effective amount of a compound that specifically inhibits the pathogen's protein synthesis via EF2.

DETAILED DESCRIPTION OF THE INVENTION

This invention provides a method for identifying and evaluating compounds having antifungal and antiparasitic activity comprising: A differential two plate assay containing genetically engineered sordarin sensitive (sS1) and resistant (sR1) strains or naturally selected sordarin resistant strains of yeast. The readout of the assay is antimicrobial activity indicated by zones of inhibition which is more apparent against the sordarin sensitive strain relative to the sordarin resistant strain.

There are two EF2 genes in *Saccharomyces cerevisiae*, EFT1 and EFT2, and at least one of these genes is required for survival. The co-isogenic strains sS1 and sR1 were constructed by a series of genetic crosses that result in strains that are disrupted for both the EFT1 and ERG6 genes. The resultant strains are made more permeable due to the erg6 disruption (ergosterol deficient), and have either a wild-type or resistant copy of EFT2 as the only source of EF2. A known number of these yeast cells are either plated in solid medium or suspended in liquid medium and test compounds or fermentation extracts are applied with the intent of identifying samples which inhibit the growth of these yeast. The cultures are incubated at a specific temperature for a set period of time to allow for the growth of the test organisms (i.e. 30° C. for 16–24 hours). Test samples of interest are those which show a differential effect on the sordarin sensitive strain(s) vs. the resistant strain(s). Those samples which are more potent against the wildtype by definition should be preventing growth via the EF2 target.

In another aspect the present invention provides a method for identifying compounds specifically inhibiting pathogenic EF2 function comprising: (a) constructing fungal or protozoan cells dependent upon heterologous EF2 from fungal and parasitic pathogens or from the host species; (b) contacting said cell with a known dilution of a test compound or a natural product extract; and (c) quantitating the minimal inhibitory concentration (MIC) of test compound to completely inhibit growth in liquid or the measurement of an inhibitory zone on a solid substrate. Test compounds or fermentation extracts of interest are those which display a differential degree of inhibition (i.e. more inhibitory activity against the wildtype vs. resistant strains of the test organisms). For example a sample which is more effective at inhibiting the growth of a yeast EF2 dependent organism vs. one that is dependent on human EF2.

The methods of the invention provides a facile and specific assay to screen compounds as potential antifungal and antiparasitic agents. It also allows for the evaluation of test compounds against the EF2 target of obligate pathogens that cannot be cultured in the laboratory.

In the present invention, EF2 may be cloned from pathogenic organisms for use in growth inhibition assays or purified from these pathogens for use in in vitro binding or translation inhibition assays. The EF2 may be from pathogenic fungi of humans, animals or plants such as Candida, Aspergillus spp., Cryptococcus spp., Erysiphe and Puccinia. It may also be from protozoan parasites such as Plasmodium sp., Eimeria sp., Cryptosporidium sp. and Toxoplasma gondii and human and other desired host eukaryotic cells.

A compound that inhibits EF2 may be one that interferes with the translation of mRNA in target organisms. Examples of compounds that inhibit EF2 include diptheria toxin and fusidic acid, however neither of these show any specificity for pathogen over host. Fusidic acid inhibits translation in many organisms by disrupting normal ribosome-EF2 interactions. The compound that inhibits EF2 is preferably labeled to allow easy quantitation of the level of interaction between the compound and the enzyme. A prefered radio-label is tritium.

The test compound may be a synthetic compound, a mixture of synthetic compounds, a crude preparation, a purified preparation or an initial extract of a natural product obtained from plant, microorganism or animal sources.

It has been found that the antifungal agent sordarin and analogs thereof inhibit protein synthesis in certain pathogenic fungi by inhibiting the fungal EF2 function.

Sordarin is an antifungal antibiotic isolated from the mould *Sordaria araneosa* (see GB 1,162,027 and *Helvetica Chimica Acta*, 1971, 51:119–20). Other compounds having the sordarin skeleton have also been reported as antifungal agents. Japanese Kokai J62040292 discloses the compound zofimarin isolated from *Zofiela marina* sp.; Japanese Kokai J06157582 discloses the compound BE-31405 isolated from Penicillium sp.; and SCH57404 is reported in *J. Antibiotics*, 1995, 48:1171–1172. Semi-synthetic sordarin derivatives are reported in PCT Applications WO96/14326 and WO96/14327.

Sordaricin, the aglycone, may be obtained from sordarin by acid hydrolysis (Hauser and Sigg, *Helvetica Chimica*

*Acta,* 1971, 51:119–20); similarly sordaricin methyl ester is obtained from sordarin methyl ester. The total synthesis of sordaricin methyl ester is reported in Kato et al, *J. Chem. Soc., Chem. Commun.,* 1993, 1002–1004, which also discloses O-methoxymethyl sordaricin methyl ester. The diacetate of 4-desformyl-4-hydroxymethyl sordaricin is disclosed in Mander and Robinson, *J. Org. Chem.,* 1991, 56(11):3395–3601. Neither sordaricin nor the reported derivatives thereof has been shown to have biological activity.

Sordarin analogs of the formula

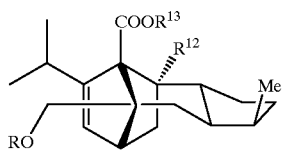

I wherein

R is
    (a) $C(=O)OR^1$,
    (b) $C(=O)NR^2R^3$,
    (c) $C(=O)R^4$,
    (d) $CH(R^2)OR^5$,
    (e) $C(R^6)(R^7)(R^8)$, (f)

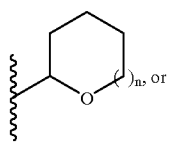

(g)

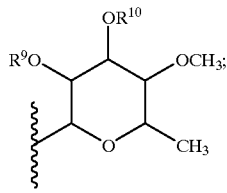

with the proviso that when $R^{12}$ is CHO, R is not (g);

$R^1$ is
    (a) $C_1$–$C_{14}$ alkyl,
    (b) $C_2$–$C_{14}$ alkenyl,
    (c) $C_2$–$C_{14}$ alkynyl,
    (d) $C_3$–$C_{20}$ cycloalkyl,
    (e) aryl or
    (f) aryl $C_{1-6}$ alkyl;

$R^2$ and $R^3$ are independently
    (a) H or
    (b) $R^1$;

$R^4$ is
    (a) H,
    (b) $R^1$ or
    (c) $-(CH_2)_mNR^2R^3$;

$R^5$ is
    (a) $R^1$ or
    (b) $-(CH_2)_xO(CH_2)_yH$;

$R^6$ is
    (a) H,
    (b) $C_1$–$C_{14}$ alkyl,
    (c) aryl,
    (d) aryl $C_{1-6}$ alkyl,
    (e) $-(CH_2)_yCHR_{11}(CH_2)_zH$,
    (f) $-(CH_2)_yC\equiv C(CH_2)_zH$,
    (g) $-(CH_2)_yC(R^7)=CH(CH_2)_zH$,
    (h) $-(CH_2)_yC\equiv C(CH_2)_mR^{11}$,
    (i) $-(CH_2)_yC(R^7)=CH(CH_2)_mR^{11}$, $R^7$ and $R^8$ are independently
    (a) H, or
    (b) $C_1$–$C_{14}$ alkyl;

$R^9$ and R10 are independently
    (a) H,
    (a) $C_1$–$C_{14}$ alkyl,
    (a) $C_2$–$C_{14}$ alkenyl,
    (a) aryl $C_{1-6}$ alkyl;

$R^{11}$ is
    (a) OH or
    $NR^2R^3$;

$R^{12}$ is
    (a) $-C(=O)R^{14}$,
    (b) $-CH=NOH$, or
    (c) $-CH_2OCH_3$;

$R^{13}$ is
    (a) H,
    (b) $-CH_2C_6H_5$,
    (c) $-CH_2CH=CH_2$, (d)

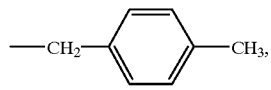

(e)

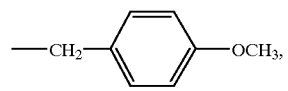

(f)

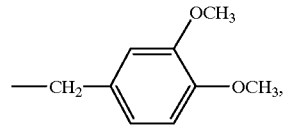

(g)

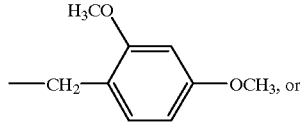

(h)

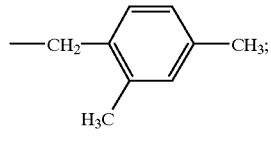

$R^{14}$ is
    (a) H,
    (b) $C_1$–$C_4$ alkyl,
    (c) $-CCl_3$,
    (d) $-CBr_3$,
    (e) $-CF_3$, or
    (f) OH;

n is 0 or 1;

m is 1–6;

x is 2–6;

y is 0–6;

z is 0–6 or a pharmaceutically or agriculturally acceptable salt thereof are disclosed in pending U.S. application Ser. No. 60/026,993 filed Oct. 7, 1996. Additional analogs of sordarin are disclosed in U.S. patent application Ser. No. 60/026,580 filed Sep. 18, 1996.

EF2 inhibitors are useful as antifungal and antiparasitic agents. As such, they may be used in the treatment and prevention of fungal and parasitic diseases in human, animals and plants. Examples of fungal diseases against which EF2 inhibitors may be used, and their respective causative pathogens, include: 1) Erysiphe, Puccinia, Septoria, Botrytis, Phytophthora, Plasmopora and other fungi which cause infections in plants and crops 2) Candida, Aspergillus, Cryptococcus, Fusarium, Penicillium and other fungi which cause fungal infections in man and animals 3) Plasmodium, Eimeria, Toxoplasma, Neospora, Cryptosporidium and other protozoa which infect man and animals.

In another aspect the present invention provides a method for the treatment of fungal or parasitic infections comprising administering to a host suffering from a fungal or parasitic infection a therapeutically effective amount of a compound which inhibits EF2 function. A therapeutically effective amount may be one that is sufficient to inhibit protein synthesis of the causative fungi or parasite.

EF2 inhibitors may be administered to a host in need of treatment in a manner similar to that used for other antifungal and antiparasitic agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of fungal and parasitic diseases in human and animals, the dosage may range from 0.01 mg/kg to 500 mg/kg. For prophylactic use in human and animals, the dosage may range from 0.01 mg/kg to 100 mg/kg.

The compositions of the present invention comprises an EF2 inhibitor and an inert carrier. The compositions may be in the form of pharmaceutical compositions for human and veterninary usage, or in the form of feed composition. The term "composition" is intended to encompass a product comprising the active ingredient(s), and the inert ingredient (s) that make up the carrier, as well as any product which results, directly or indirectly, from combination, complexation or aggregation of any two or more of the ingredients, or from dissociation of one or more of the ingredients, or from other types of reactions of one or more of the ingredients. The composition of the present invention thus includes a composition when made by admixing an EF2 inhibitor and inert carrier.

The pharmaceutical compositions of the present invention comprise an EF2 inhibitor as an active ingredient, and may also contain a pharmaceutically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, an EF2 inhibitor can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, EF2 inhibitors may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

EXAMPLES

The following non-limiting, examples are provided to illustrate the invention. The assays may be ran in 96 well or other appropriate sized plates or in the appropriate liquid medium.

Preparation of Materials Used in the Examples

Compound I of the formula

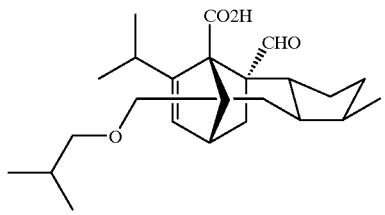

Compound I is a sordarin analog. The preparation of Compound I is described in U.S. application Ser. No. 60/026,993 filed Oct. 7, 1996.

Construction of Yeast Strain

The yeast strain YEFD12h/pURA3-EFT1, that is deleted for both chromosomal copies of genes which encode EF2, has been obtained from the laboratory of James Bodley (Phan et al., Journal of Biological Chemistry (1993). 268:8665–8668). This strain also contains an episomal copy of a gene encoding EF2, and is essential for cell viability. Yeast strains expressing EF2 genes from pathogens of interest may be constructed by (1) transforming YEFD12h/pURA3-EFT1 with yeast expression plasmids that contain heterologous EF2 encoding genes, and (2) evicting the plasmid containing the native EF2 gene from the cell. This may be used in the growth inhibition assay described below.

Example 1

Competitive Binding Assay

A competitive assay can be performed involving the displacement of a radiolabeled compound with specificity for pathogen EF2 such as $^3$H-Compound I binding to *Saccharomyces cerevisiae* EF2 in crude S30 extracts. As proof of the specificity of inhibitor found with the S30 binding assay, binding competition can also be performed with purified EF2 in the presence of washed ribosomes.

Specific binding of $^3$H-Compound I is found with Saccharomyces S30 extracts and requires the presence of ribosomes as well as EF2. The binding is displaceable by unlabelled L-793,422, sordarin and analogs. No binding is seen with mammalian cell or wheat germ S30 extracts. The specificity of $^3$H-L793,422 for yeast resides in the EF2 molecule since substitution of yeast ribosomes with either rat or wheat germ has no effect on binding, while substitution of yeast EF2 with rat or wheat germ EF2 abolishes binding.

Materials:
Sephadex G-75 (G-75-120)
Mini column: GS-QS quick-sep micro column (Isolab)
Mini vials (4 ml)
Scintiverse
Buffer A: 50 mM Tris-HCl PH 7.5,150 mM NaCl,10 mM MgCl 2,1 mM EDTA
Buffer B: 50 mMTris-HCl PH 7.5,10 mM MgCl 2, 1 mM EDTA
GTP-γ-s (Sigma)
Yeast S-30, prepared as below.
3H-Compound I (20 mCi/mg, 8000 mCi/mmol; 0.004 mg/ml)

In a microfuge tube 100 μl assay mixture contains: 10 μg yeast S-30, 25 μM GTP-γ-s (0.5 μl of 5 mM stock), dilutions of agent to be examined for ability to compete for binding and Buffer B to bring volume to 98 µl. Vortex and incubate at room temperature 5 min. Add 2 µl $^3$H-Compound I (1:20 dilution in water). Vortex and incubate for 20–30 min.

To a Sephadex G-75 column was pre-soaked in Buffer A (20 gm/400 ml) several hours. Mini columns were packed with G-75 precisely to the mark line (~1.6 ml) and allowed to settle by washing with 2 ml Buffer A.

The 100 µl incubated mixtures are loaded onto G-75 columns (no collection) As soon as the sample has entered the gel bed (approximately 20 sec), 0.7 ml Buffer A is added and eluate is collected in mini vials 3 ml Scintiverse is added and vials counted.

Saccharomyces S30 extract

A *Saccharomyces cerevisiae* strain containing wild-type EF2 is inoculated into medium containing in g/l: 10 g Bacto Yeast Extract, 20 g Bacto Peptone, 20 g dextrose and 60 mg adenine and incubated with shaking at 30° C. until mid to late logarithmic phase (A600~2). The cells are harvested and washed twice with water. Pellets may be stored at −70° C. indefinitely prior to disruption. For breakage, cells are resuspended in 2 vol of buffer containing 50 mM Tris-Cl pH 7.4, 10% (wt/vol) glycerol, 2 mM $MgCl_2$, 2 mM dithiothreitol, 1 mM phenylmethylsulfonyl fluoride and broken by prolonged agitation with acid-washed 0.5 mm glass beads. The supernatant is centrifuged at 30 g for 15 min to sediment cell debris.

Results

10 µg S30 extract from wild-type Saccharomyces binds approximately 0.5 pmol labelled sordarin analog $^3$H-Compound I. This is displaced with an IC50 of 3 ng/ml by sordarin or its more active analogs.

Binding Assay with Purified Components

This assay involves the same procedure as disclosed above substituting 0.4 A260 units salt-washed *S. cerevisiae* ribosomes and 1 pmol purified EF2 for the 10 µg S30 in the above assay. The ribosomes and EF2 are both prepared by published methods (L. Skogerson, Methods in Enzymology, Vol LX,p676–685).

As with the S30 binding assay, this assay may be used to either identify the component binding drug, or to examine competition by unknown agents.

Results 0.65 pmol purified Saccharomyces EF2 plus 4 pmol purified Saccharomyces ribosomes binds approximately 0.6 pmol labelled compound, with similar displacement (IC50 3 ng/ml) by active analogs. Replacement of Saccharomyces ribosomes by those of either rat liver or wheat germ does not reduce binding. However, replacement of Saccharomyces EF2 by EF2 from either of these sources, abolishes binding to background levels.

Example 3

Measurement of Protein Synthesis in Pathogen/Host

Another method of identifying specific inhibitors of the pathogen protein synthesis is to measure the incorporation of radio-labeled amino acids into TCA precipitable proteins in the pathogen and the host. Test samples with activity that indicates pathogen selectivity can then be further screened in the more specific EF2 assays.

Reconstituted Protein Synthesis

This assay involves inhibition of polyphenylalanine synthesis in a reconstituted in vitro translation system Ribosomes, EF1, EF2 and EF3 are purified from *Saccharomyces cerevisiae,* and the assay is performed, as described in (L. Skogerson, Methods in Enzymology, Vol LX,p676–685).

Sordarin, its analogs and any unknowns may be titrated in this assay and an $IC_{50}$ value determined for inhibition. Ribosomes and EF2 from other eukaryotic systems may be purified as described in the literature. When EF2 from rat liver (prepared as described by J. F. Collins, F. Raeburn and E. S. Maxwell. J. Biol. Chem:246 pp1049–1064 [1971]) or wheat germ (prepared as described by S. J. Lauer, E. Burks, J. D. Irvin and J. M. Ravel. J. Biol. Chem. 259: pp1644–1648 [1984]) is substituted for yeast EF2 in the *S. cerevisiae system,* no inhibition is found for the sordarin class of compounds up to levels limited by drug solubility. On the other hand, substitution of yeast ribosomes by rat liver or wheat germ ribosomes does not affect the ability of the sordarin class to inhibit the reconstituted translation system.

Results

| | $IC_{50}$ for inhibition | | |
|---|---|---|---|
| | Source of ribosomes | | |
| Source of EF2 | Yeast | Mammalian | Wheat Germ |
| Yeast | 0.01 µg/ml | 0.01 µg/ml | 0.02 µg/ml |
| Mammalian | >50 µg/ml | >50 µg/ml | >50 µg/ml |
| Wheat Germ | >50 µg/ml | >50 µg/ml | >50 µg/ml |

Example 4

Growth Inhibition Assay I

An assay has been developed to identify antifungal compounds with sordarin like activities using *S. cerevisiae* as a surrogate organism. It consists of a two plate differential zone assay using sordarin sensitive (sS1) and resistant strains (sR1) that contain an erg6 deletion, which increases membrane permeability and facilitates the uptake of various substances. In this screen, active compounds show a clear zone on the sensitive strain plate and no zone for the resistant strain plate.

Methods

Approximately 1×10$^6$ cells per ml are added to growth medium containing 2% agar. Medium and cells are mixed, poured into plates, and allowed to solidify. Test compounds or fermentation extracts are applied with the intent of identifying samples which inhibit the growth of these yeast. The cultures are incubated at 30° C. for 16–24 hours. A similar assay can also be run in a high-throughput microtiter format by inoculating cells into liquid growth medium containing test compounds or fermentation extracts. Active compounds can be identified by assaying for growth inhibition, which can be determined by measuring the optical density of the individual cultures.

Results 0.5 µg of sordarin gives a clear zone of 20 mm with the sensitive strain and no zone with the resistant strain.

What is claimed is:

1. A method for identifying a test compound which specifically inhibits pathogen EF2 over host EF2 comprising the steps of:

(a) adding a compound to a genetically engineered eukaryotic organism sensitive to pathogen selective effects on EF2 function;

(b) determining whether said compound inhibits protein synthesis using a growth inhibition assay; and (c) correlating protein synthesis and pathogen EF2 inhibition.

2. The method of claim 1 wherein said eukaryotic organism is *Saccharomyces cerevisiae* deleted or mutated for EF2.

3. A method for identifying a compound which specifically inhibits pathogen EF2 over host EF2 comprising the steps of:

(a) constructing fungal or protozoan cells that express a heterologous EF2 from fungal and parasitic pathogens;

(b) inoculating the cells of step (a) into liquid or onto solid growth medium containing test compounds or fermentation extracts;

(c) quantitating the minimal inhibitory concentration (MIC) of the test compound to completely inhibit growth in a liquid medium; or (d) quantitating the size of any existing plaques on the solid medium; and (e) correlating the MIC of the test compound in the liquid medium with pathogen EF2 inhibition to determine the effect of the test compound on pathogen EF2 inhibition.

4. The method of claim 3 wherein the cells are inoculated onto a solid growth medium and the inhibition of growth of the test compound is determined by measuring the plaques formed on the solid substrate upon which the cells are inoculated.

5. The method of claim 3 wherein the cells are inoculated into liquid growth medium and the inhibition of growth of the test compound is a measurement of the optical density of growth in the liquid.

6. A method for identifying a compound which specifically inhibits pathogen EF2 over host EF2 comprising the steps of:

(a) plating a known dilution of cells expressing a heterologous EF2 on an appropriate medium;

(b) contacting the cells of step (a) with a known dilution of a test compound or natural product extract;

(c) incubating said cells at about 30° C. for about 16–24 hours; and (d) quantitating the percent of growth inhibition specific for loss of EF2 function due to the test compound or natural product extract.

7. A method for identifying a compound having antifungal activity which inhibits pathogen EF2 over host EF2 comprising the steps of:

(a) contacting pathogen EF2 or an extract containing pathogen EF2 with a known amount of a labeled compound that interacts with pathogen EF2;

(b) contacting said EF2 or said extract with a known dilution of a test compound or a natural product extract;

(c) quantitating the percent inhibition of interaction of said labeled compound with pathogen EF2 induced by said test compound; and (d) correlating binding inhibition to pathogen EF2 by said test compound with fungal growth.

* * * * *